US009131964B2

(12) United States Patent
Blain et al.

(10) Patent No.: US 9,131,964 B2
(45) Date of Patent: Sep. 15, 2015

(54) TRANSVERSE CONNECTORS

(71) Applicant: Spinal Elements, Inc., Carlsbad, CA (US)

(72) Inventors: Jason Blain, Encinitas, CA (US); Greg Martin, Encinitas, CA (US); Steven Howard, San Diego, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 14/445,535

(22) Filed: Jul. 29, 2014

(65) Prior Publication Data

US 2014/0336707 A1 Nov. 13, 2014

Related U.S. Application Data

(63) Continuation of application No. 12/764,850, filed on Apr. 21, 2010, now Pat. No. 8,828,055.

(60) Provisional application No. 61/172,116, filed on Apr. 23, 2009.

(51) Int. Cl.
*A61B 17/70* (2006.01)

(52) U.S. Cl.
CPC ................................ *A61B 17/7052* (2013.01)

(58) Field of Classification Search
CPC .................................. A61B 17/7049–17/7052
USPC .................................................. 606/250–253
See application file for complete search history.

(56) References Cited

U.S. PATENT DOCUMENTS

| 5,281,222 A | 1/1994 | Allard et al. |
| 5,312,405 A | 5/1994 | Korotko et al. |
| 5,545,167 A | 8/1996 | Lin |
| 5,624,442 A | 4/1997 | Mellinger et al. |

(Continued)

FOREIGN PATENT DOCUMENTS

| EP | 1302169 | 4/2003 |
| WO | WO 02-091931 | 11/2002 |

(Continued)

OTHER PUBLICATIONS

Dec. 30, 2010 International Search Report and Written Opinion for International Application No. PCT/US2010/031958 filed on Apr. 21, 2010.

(Continued)

*Primary Examiner* — Eduardo C Robert
*Assistant Examiner* — Jacqueline Johanas
(74) *Attorney, Agent, or Firm* — Knobbe, Martens, Olson & Bear, LLP

(57) ABSTRACT

Devices and methods are disclosed for treating the vertebral column. One embodiment provides a transverse connector for vertebral fixation systems comprising a first connector body comprising a first engaging member for engaging a first elongate member and a first locking member, a second connector body comprising a second engaging member for engaging a second elongate member, and a transverse rod coupled to the first connector body and the second connector body, thereby forming an articulation between a first end of the transverse rod and the first connector body, wherein the first locking member is configured to secure both the articulation and the first elongate member to the first connector body.

19 Claims, 9 Drawing Sheets

(56) References Cited

U.S. PATENT DOCUMENTS

| | | | |
|---|---|---|---|
| 5,683,393 A | 11/1997 | Ralph | |
| 5,688,272 A | 11/1997 | Montague et al. | |
| 5,716,355 A | 2/1998 | Jackson et al. | |
| 5,743,911 A | 4/1998 | Cotrel | |
| 5,776,135 A | 7/1998 | Errico et al. | |
| 5,947,966 A | 9/1999 | Drewry et al. | |
| 5,980,521 A | 11/1999 | Montague et al. | |
| 5,980,523 A | 11/1999 | Jackson | |
| 6,083,226 A | 7/2000 | Fiz | |
| 6,113,600 A | 9/2000 | Drummond et al. | |
| 6,171,311 B1 | 1/2001 | Richelsoph | |
| 6,217,578 B1 | 4/2001 | Crozet et al. | |
| 6,234,705 B1 | 5/2001 | Troxell | |
| 6,238,396 B1 | 5/2001 | Lombardo | |
| 6,261,288 B1 | 7/2001 | Jackson | |
| 6,283,967 B1 | 9/2001 | Troxell | |
| 6,302,882 B1 | 10/2001 | Lin et al. | |
| 6,306,137 B2 | 10/2001 | Troxell | |
| 6,328,740 B1 | 12/2001 | Richelsoph | |
| 6,328,741 B1 | 12/2001 | Richelsoph | |
| 6,402,751 B1 | 6/2002 | Hoeck et al. | |
| 6,413,258 B1 | 7/2002 | Bernhardt | |
| 6,524,310 B1 | 2/2003 | Lombardo et al. | |
| 6,554,832 B2 | 4/2003 | Shluzas | |
| 6,595,992 B1 | 7/2003 | Wagner et al. | |
| 6,616,668 B2 | 9/2003 | Altarac et al. | |
| 6,736,817 B2 | 5/2004 | Troxell et al. | |
| 6,752,807 B2 | 6/2004 | Lin et al. | |
| 6,761,721 B2 | 7/2004 | Burgess et al. | |
| 6,783,526 B1 | 8/2004 | Lin et al. | |
| 6,802,844 B2 | 10/2004 | Ferree | |
| 6,866,664 B2 | 3/2005 | Schar et al. | |
| 6,872,208 B1 | 3/2005 | McBride et al. | |
| 6,875,211 B2 | 4/2005 | Nichols et al. | |
| 6,887,241 B1 | 5/2005 | McBride et al. | |
| 7,029,474 B2 | 4/2006 | Richelsoph et al. | |
| 7,104,993 B2 | 9/2006 | Baynham et al. | |
| 7,122,036 B2 | 10/2006 | Vanacker | |
| 7,137,986 B2 | 11/2006 | Troxell et al. | |
| 7,485,132 B1 | 2/2009 | McBride et al. | |
| 7,569,069 B2 | 8/2009 | Sasing et al. | |
| 7,744,632 B2 | 6/2010 | Usher | |
| 7,780,704 B2 | 8/2010 | Markworth et al. | |
| 7,922,747 B2 | 4/2011 | Kirschman | |
| 8,075,594 B2 | 12/2011 | Purcell | |
| 8,167,908 B2 | 5/2012 | Ely et al. | |
| 8,262,701 B2 | 9/2012 | Rathbun et al. | |
| 8,262,702 B2 | 9/2012 | Giger et al. | |
| 8,277,489 B2 | 10/2012 | Saidha et al. | |
| 8,480,712 B1 | 7/2013 | Samuel et al. | |
| 8,491,642 B2 | 7/2013 | Marino et al. | |
| 8,870,921 B2 * | 10/2014 | Michielli et al. | 606/250 |
| 2002/0143327 A1 | 10/2002 | Shluzas | |
| 2002/0169448 A1 | 11/2002 | Vanacker | |
| 2003/0114853 A1 | 6/2003 | Burgess et al. | |
| 2004/0260285 A1 | 12/2004 | Steib et al. | |
| 2004/0260287 A1 | 12/2004 | Ferree | |
| 2005/0004574 A1 | 1/2005 | Muckter | |
| 2005/0038425 A1 | 2/2005 | Werding et al. | |
| 2005/0080416 A1 | 4/2005 | Ryan et al. | |
| 2005/0090821 A1 | 4/2005 | Berrevoets et al. | |
| 2005/0096654 A1 | 5/2005 | Lin | |
| 2005/0107789 A1 | 5/2005 | Sweeney | |
| 2005/0228377 A1 | 10/2005 | Chao et al. | |
| 2006/0058789 A1 | 3/2006 | Kim et al. | |
| 2006/0064091 A1 | 3/2006 | Ludwig et al. | |
| 2006/0064093 A1 | 3/2006 | Thramann et al. | |
| 2006/0129150 A1 | 6/2006 | Suzuki et al. | |
| 2006/0195095 A1 | 8/2006 | Mueller et al. | |
| 2006/0206114 A1 | 9/2006 | Ensign et al. | |
| 2006/0217712 A1 | 9/2006 | Mueller et al. | |
| 2006/0241598 A1 | 10/2006 | Khalili | |
| 2006/0241769 A1 | 10/2006 | Gordon et al. | |
| 2006/0241771 A1 | 10/2006 | Gordon et al. | |
| 2006/0247626 A1 | 11/2006 | Taylor et al. | |
| 2006/0247635 A1 | 11/2006 | Gordon et al. | |
| 2006/0247779 A1 | 11/2006 | Gordon et al. | |
| 2006/0259038 A1 | 11/2006 | Cordaro | |
| 2006/0271045 A1 | 11/2006 | Hubbard et al. | |
| 2006/0271051 A1 | 11/2006 | Berrevoets et al. | |
| 2007/0016197 A1 | 1/2007 | Woods et al. | |
| 2007/0043358 A1 | 2/2007 | Molz, IV | |
| 2007/0049932 A1 | 3/2007 | Richelsoph et al. | |
| 2007/0055239 A1 | 3/2007 | Sweeney et al. | |
| 2007/0055244 A1 | 3/2007 | Jackson | |
| 2007/0083201 A1 | 4/2007 | Jones et al. | |
| 2007/0093832 A1 | 4/2007 | Abdelgany | |
| 2007/0123860 A1 | 5/2007 | Francis et al. | |
| 2007/0161999 A1 | 7/2007 | Biedermann et al. | |
| 2007/0173829 A1 | 7/2007 | Drewry et al. | |
| 2007/0213723 A1 | 9/2007 | Markworth et al. | |
| 2007/0219556 A1 | 9/2007 | Altarac et al. | |
| 2007/0225712 A1 | 9/2007 | Altarac et al. | |
| 2007/0225713 A1 | 9/2007 | Altarac et al. | |
| 2007/0270813 A1 | 11/2007 | Garamszegi | |
| 2007/0288002 A1 | 12/2007 | Carls et al. | |
| 2007/0288003 A1 | 12/2007 | Dewey et al. | |
| 2007/0293862 A1 | 12/2007 | Jackson | |
| 2008/0015588 A1 | 1/2008 | Hawkes | |
| 2008/0021455 A1 | 1/2008 | Chao et al. | |
| 2008/0021456 A1 | 1/2008 | Gupta | |
| 2008/0021464 A1 | 1/2008 | Morin et al. | |
| 2008/0103507 A1 | 5/2008 | Purcell | |
| 2008/0109039 A1 | 5/2008 | Michielli et al. | |
| 2008/0177315 A1 | 7/2008 | Usher | |
| 2008/0306538 A1 | 12/2008 | Moore | |
| 2009/0018586 A1 | 1/2009 | Butler et al. | |
| 2009/0088800 A1 | 4/2009 | Blain et al. | |
| 2009/0105763 A1 * | 4/2009 | Kirschman | 606/264 |
| 2009/0312799 A1 | 12/2009 | Sasing et al. | |
| 2009/0326588 A1 | 12/2009 | Felix et al. | |
| 2010/0057131 A1 | 3/2010 | Ely et al. | |
| 2010/0063546 A1 | 3/2010 | Miller et al. | |
| 2010/0094345 A1 | 4/2010 | Saidha et al. | |
| 2010/0204733 A1 | 8/2010 | Rathbun et al. | |
| 2011/0137345 A1 * | 6/2011 | Stoll et al. | 606/251 |
| 2012/0004688 A1 | 1/2012 | Marino et al. | |
| 2012/0035659 A1 | 2/2012 | Barrus et al. | |
| 2012/0226316 A1 | 9/2012 | Dant et al. | |

FOREIGN PATENT DOCUMENTS

| | | |
|---|---|---|
| WO | WO 2008-008853 | 1/2008 |
| WO | WO 2008-045477 | 6/2008 |
| WO | WO 2009-042653 | 4/2009 |

OTHER PUBLICATIONS

International Search Report and Written Opinion for International Application No. PCT/US2010/031958 (Foreign counterpart to present application) dated Aug. 11, 2013.

* cited by examiner

TRANSVERSE CONNECTORS

CROSS-REFERENCE TO RELATED APPLICATIONS

The present application is a continuation of U.S. patent application Ser. No. 12/764,850 filed on Apr. 10, 2010, which claims priority under 35 U.S.C. §119(e) to U.S. Provisional Application No. 61/172,116 filed on Apr. 23, 2009. The disclosure of U.S. patent application Ser. No. 12/764,850 filed on Apr. 10, 2010 is hereby incorporated by reference herein in its entirety.

BACKGROUND OF THE INVENTION

1. Field of the Invention

The present invention relates generally to transverse connectors used in spinal fixation systems. The invention comprises assemblies that are coupled to spinal rods, plates, or other elongate members to provide stability to a construct. The invention may be configured so that multiple transverse connectors may be used along the vertebral column.

2. Description of the Related Art

Advancing age, as well as injury, can lead to degenerative changes in the bones, discs, joints and ligaments of the spine, producing pain and instability. Under certain circumstances, alleviation of the problems can be provided by performing spinal fusion. Spinal fusion is a surgical technique where two or more vertebrae of the spinal column are fused together to eliminate the motion between the fused vertebrae. Spinal fusion is used to treat conditions where the spine exhibits instability. Spine instability may result from causes such as fracture, scoliosis and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of fixation systems for achieving spinal fusion is well established. One of the more common fixation systems is the pedicle screw fixation system. In this fixation system, pedicle screws are inserted into two or more vertebrae and interconnected with a rod or other elongate member. The screws are rigidly connected to the elongate member so that the fixation system greatly reduces motion between the adjoining vertebrae. Multiple fixation systems may be utilized to achieve greater strength and stability. Other types of fixation systems use different vertebrae attachment devices, including but not limited to, transverse process hooks, sub-laminar hooks, pedicle hooks, fixation plates and other similar devices.

It is well known in the art that coupling multiple fixation systems with a transverse connector also increases strength and stability of the assembly. A transverse connector is used to span the distance between two elongate members. Ideally, the fixation system is implanted in the body so that the two elongate members are substantially parallel to each other in a single plane. This permits the use of a simple transverse connector that need only be adjustable in length, along its longitudinal axis. However, due to variations in body geometries and implanting inconsistencies, the elongate members are rarely parallel in practice. The elongate members may be co-planar but not parallel, or may not be co-planar, or both not co-planar nor parallel. In the past, this problem was addressed by forcefully bending the elongate members or the transverse connector to accommodate for the misalignment of the elongate members. This solution is not optimal because it introduces misalignments that possibly compromise the strength and stability of the assembly. Additionally, it could weaken the mechanical properties of the elongate member or the transverse connector.

Prior inventions addressed this problem through the use of a transverse connector with greater adjustability. U.S. Pat. No. 5,980,523 discloses a transverse connector with separable pieces that are assembled together with separate screw fasteners to accommodate for non-parallel elongate members. The disadvantage with this invention is the number of separable pieces, which are difficult to assemble in the clinical environment, especially considering the miniature sizes of some of the pieces. Surgeons may also risk losing pieces within the patient's body cavity during implantation.

Further advancements solved this problem with the invention of a one-piece transverse connector, but there still remains some shortcomings. For example, U.S. Pat. No. 6,736,817 discloses a one-piece transverse connector that is adjustable for convergent or divergent elongate members, non-coplanar elongate members, and variations in distances between elongate members. The adjustment for convergence or divergence is accomplished through a joint placed between two coupling hooks that attach to elongate members. The joint comprises of two mating surfaces, each with teeth that allows the two ends of the transverse connector to hinge with respect to each other at various angles. The hinge joint is locked with a screw fastener. However, the disadvantage of this design is the complexity of the additional screw. The added screw introduces an additional component for possible failure or user error. Also, the additional weight and bulk of the hinge joint is another drawback of the design. The vertebral fixation assembly may be placed in the human body for extended periods of time. Any tiny additional weight or bulk of the fixation assembly can translate into greater discomfort for the patient. Thus, it is advantageous for the vertebral fixation assembly to be as compact as possible to minimize its intrusion in the body.

As a consequence of the foregoing, there remains a need for improved adjustable transverse connectors with simple, compact adjustments.

SUMMARY OF THE INVENTION

The present invention relates generally to transverse connectors used in spinal fixation systems.

One embodiment provides a transverse connector for vertebral fixation systems comprising a first connector body comprising a first engaging member for engaging a first elongate member and a first locking member, a second connector body comprising a second engaging member for engaging a second elongate member, and a transverse rod coupled to the first connector body and the second connector body, thereby forming an articulation between a first end of the transverse rod and the first connector body, wherein the first locking member is configured to secure both the articulation and the first elongate member to the first connector body.

The above embodiments and methods of use are explained in more detail below.

BRIEF DESCRIPTION OF THE DRAWINGS

The structure and method of using the invention will be better understood with the following detailed description of embodiments of the invention, along with the accompanying illustrations, in which.

DETAILED DESCRIPTION OF THE PREFERRED EMBODIMENT

Advancing age, as well as injury, can lead to degeneration in the bones, discs, joints, and ligaments of the spine producing pain from nerve root compression. Under certain circumstances, alleviation of pain can be provided by performing a spinal fusion. Spinal fusion is a procedure that involves joining two or more adjacent vertebrae so that they no longer are able to move relative to each other.

A. Anatomy of the Spine

Figure 1:
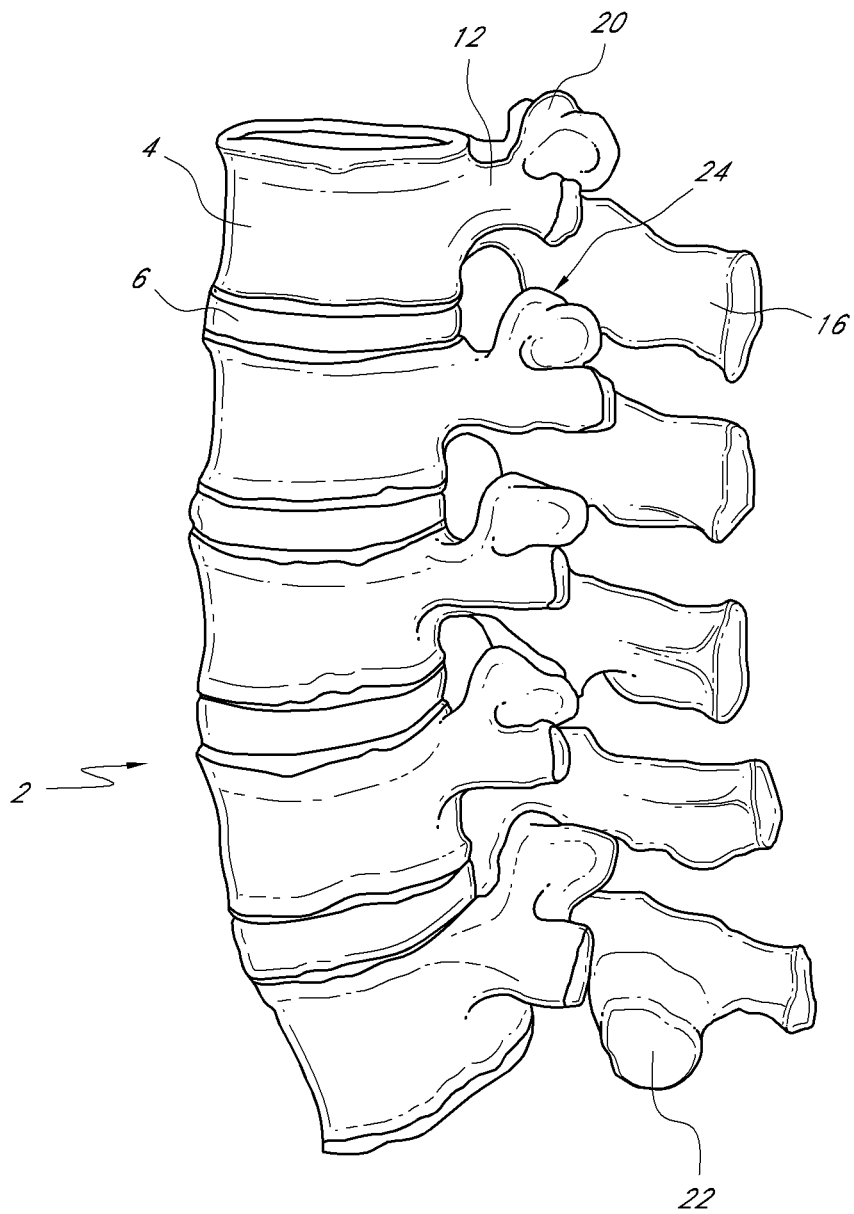
FIG. 1 is a lateral elevational view of a portion of the vertebral column.
Figure 2A:
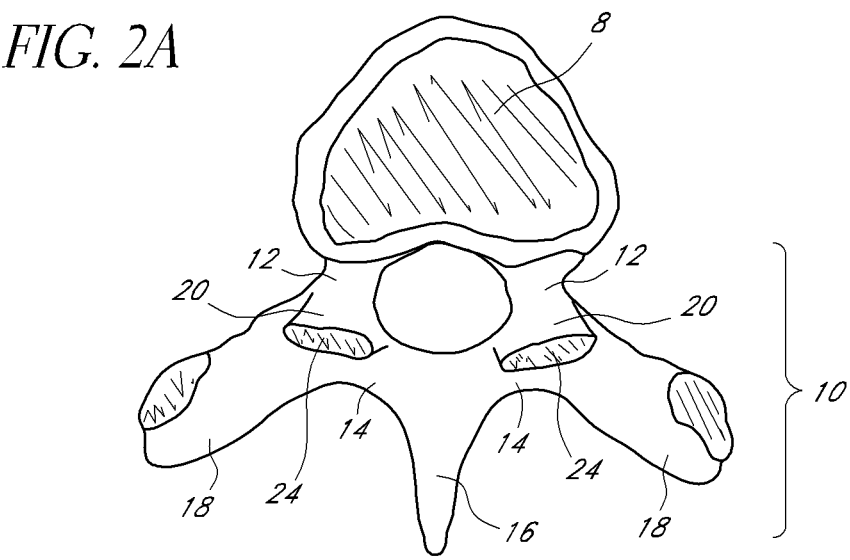
FIGS. 2A and 2B are superior and lateral elevational views of a thoracic vertebra.
Figure 2B:
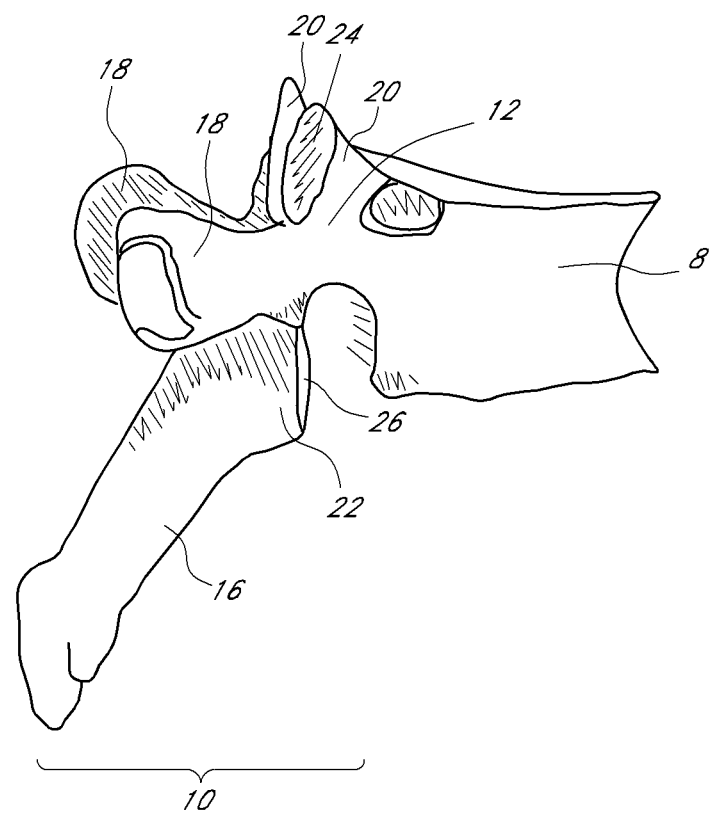

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-L5), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae.

Figure 3:
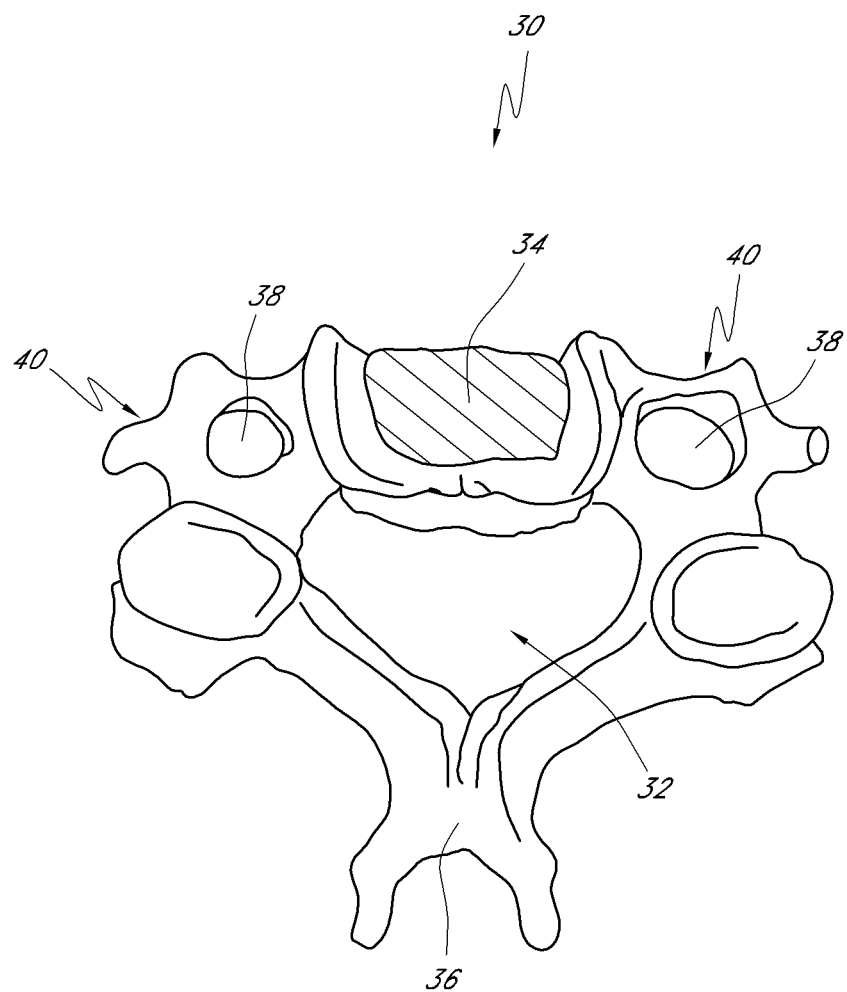
FIG. 3 illustrates a superior elevational view of a cervical vertebra.

The typical cervical vertebrae 30, shown in FIG. 3, differ from the other vertebrae with relatively larger spinal canals 32, oval shaped vertebral bodies 34, bifid spinous processes 36 and foramina 38 in their transverse processes 40. These foramina transversaria 38 contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

Figure 4:
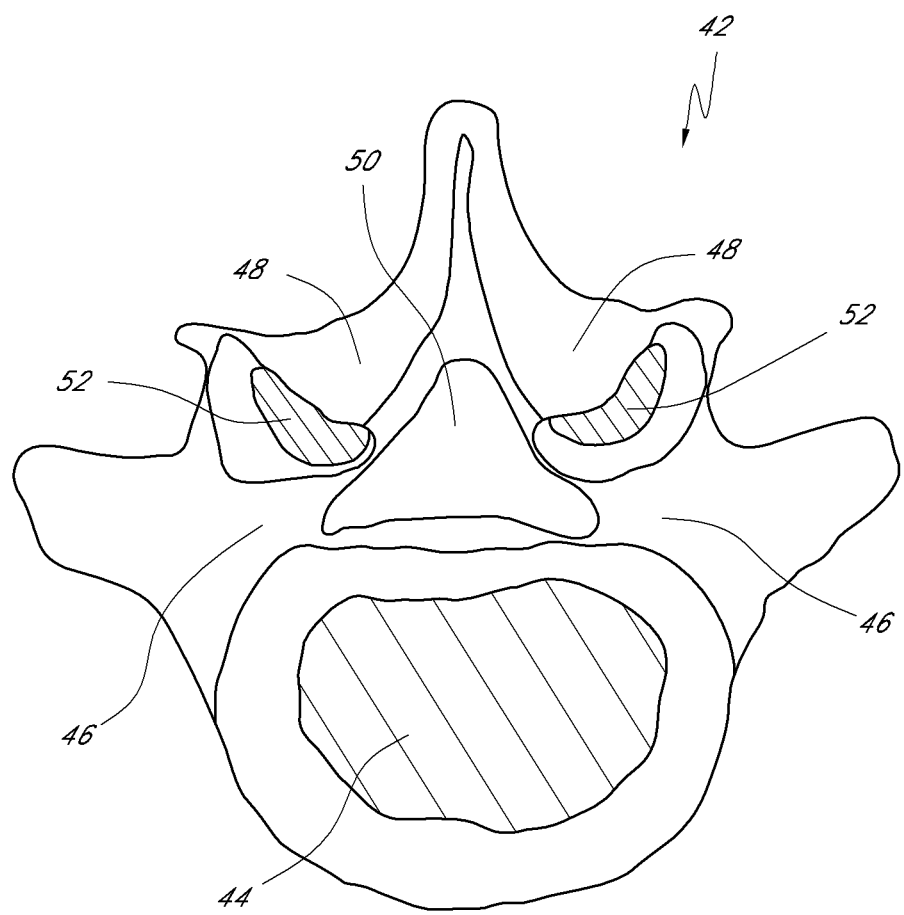
FIG. 4 represents a superior elevational view of a lumbar vertebra.

Referring to FIG. 4, the typical lumbar vertebrae 42 is distinguishable from the other vertebrae by the absence of foramina transversaria and the absence of facets on the surface of the vertebral body 44. The lumbar vertebral bodies 44 are larger than the thoracic vertebral bodies and have thicker pedicles 46 and laminae 48 projecting posteriorly. The vertebral foramen 50 is triangular in shape and larger than the foramina in the thoracic spine but smaller than the foramina in the cervical spine. The superior 52 and inferior articular processes (not shown) project superiorly and inferiorly from the pedicles, respectively.

B. Transverse Connector

Figure 5:
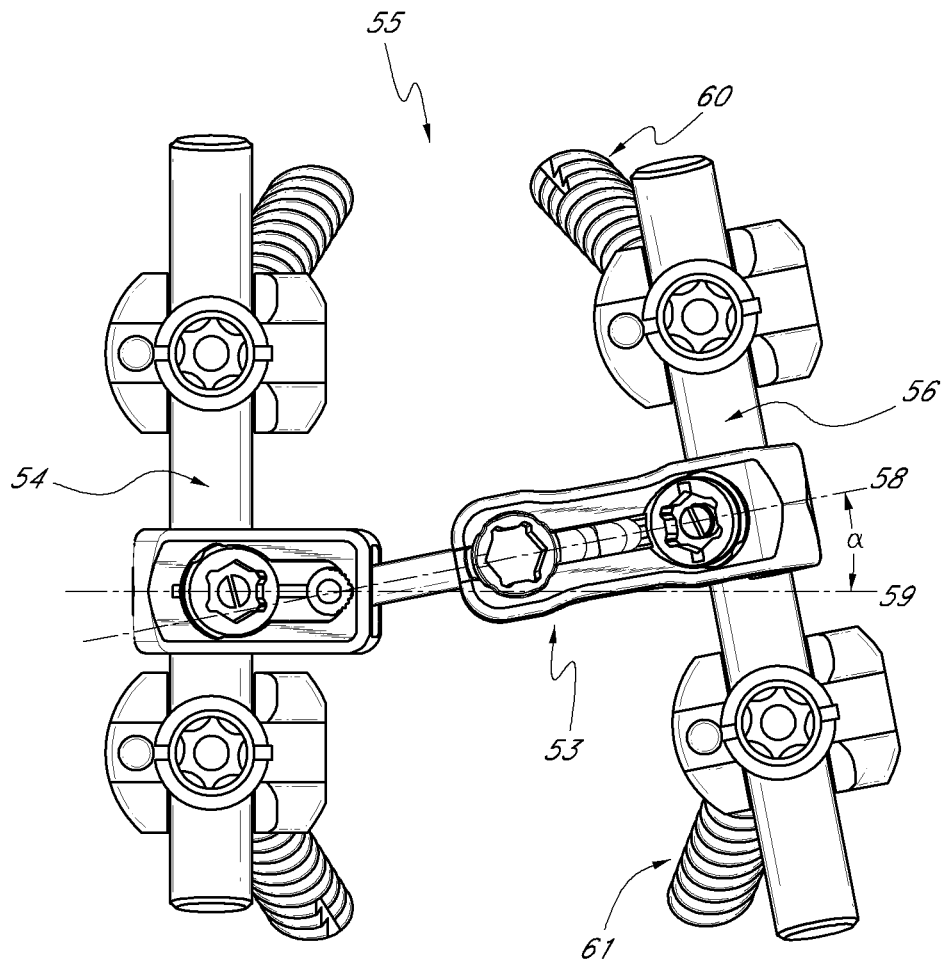
FIG. 5 is a top plan view of one embodiment of a vertebral fixation assembly.

FIG. 5 shows one embodiment of a vertebral fixation system 55, comprising a transverse connector 53 connecting a first elongate member 54 and a second elongate member 56. In some embodiments, the elongate members 54 and 56 are coupled to the vertebral column using attachment devices, such as pedicle screws. For example, a first pedicle screw 60 may be attached to a pedicle of a first vertebra and a second pedicle screw 61 may be attached to a pedicle of a second vertebra. Although depicted as pedicle screws in FIG. 5, the means for coupling the elongate members 54 and 56 to the vertebral column can be any attachment device that can couple an elongate member to a vertebra. For example, in other embodiments, the attachment devices may be hooks, clamps or other fastening device. The elongate member may be any rigid member capable of coupling to and stabilizing the vertebral column, such as a spinal rod. In some embodiments, the elongate members 54 and 56 may be rectangular bars, polygonal bars, I-beams, or any other device suitable for connecting the pedicle screws.

Figure 6:
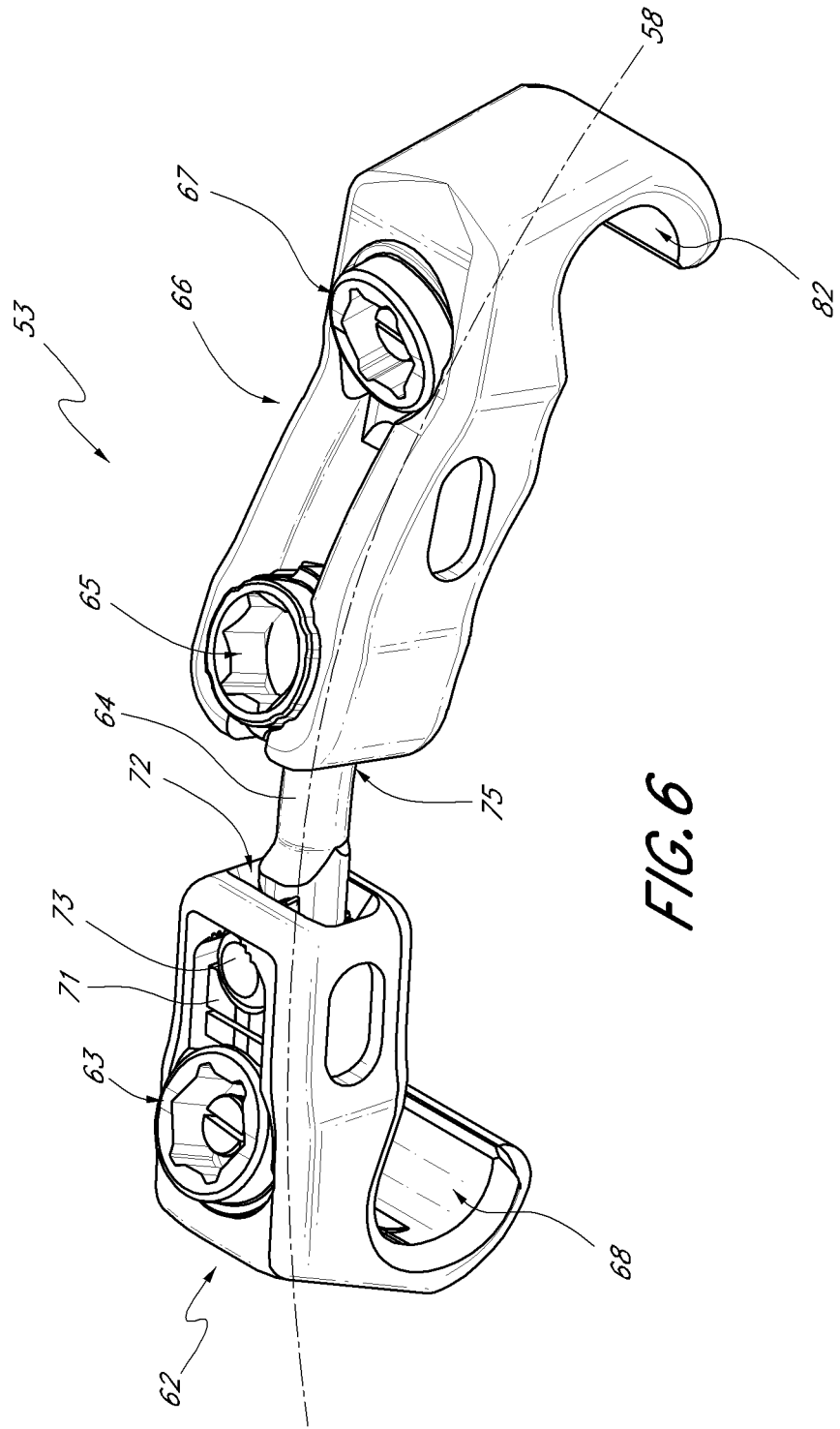
FIG. 6 is a top perspective view of one embodiment of an adjustable transverse connector.

The two elongate members are coupled to each other using a transverse connector 53. In some embodiments, the transverse connector has generally a curved shape to allow for the posterior arch of the vertebral column. The transverse connector 53 can be comprised of any material that is suitable for orthopedic applications, such as titanium, stainless steel, metal alloys, plastics, or other material compatible for use in the body. FIG. 6 shows one embodiment of the transverse connector 53, which comprises a first connector body 62 coupled to a second connector body 66 via a transverse rod 64. The transverse rod 64 comprises an end with a pivot joint 73 and a projection end 75. The end with a pivot joint 73 is configured to couple to the first connector body 62, thereby forming an articulation between the first connector body 62 and the transverse rod 64. The projection end 75 of the transverse rod 64 is configured to couple to the second connector body 66. The transverse connector 53 spans the distance between two elongate members and may be used to add stability, such as torsional stability, to the vertebral fixation system 55. In some embodiments, the transverse connector 53 is adjustable in length and can adapt for multi axial rotational differences in the orientations of the elongate members.

Figure 7:
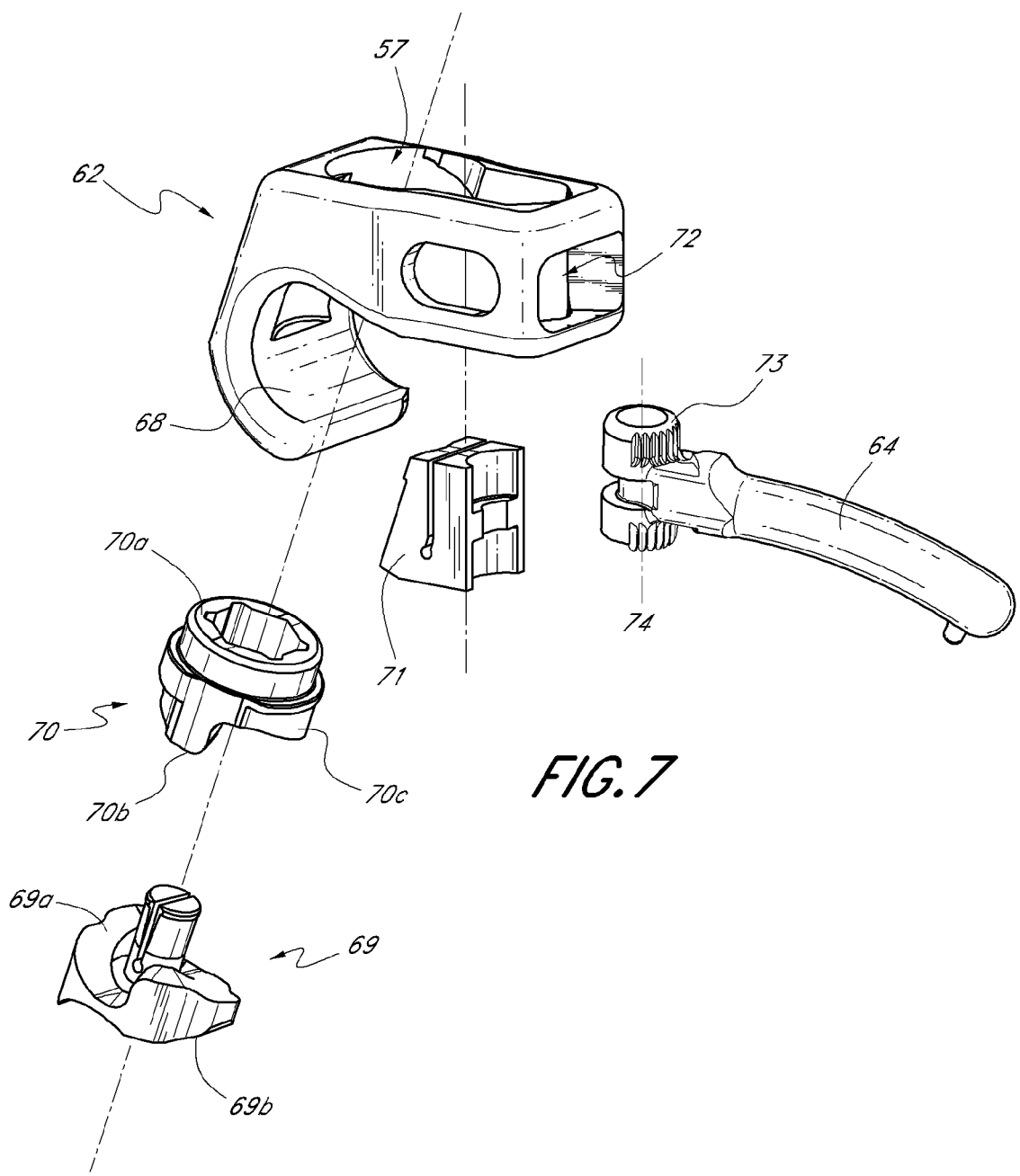
FIG. 7 is an exploded view of one embodiment of a rod connector with an articulation and a first locking member.

The first connector body 62 comprises a first locking member 63 and a first engaging member 68. In some embodiments, the first connector body 62 further comprises a pushing member 71. As shown in FIG. 7, in some embodiments, the first connector body 62 comprises a first engaging member 68 toward one end for engaging the first elongate member 54 to the first connector body 62. The first connector body 62 also comprises a through bore 57 from a first surface of the connector body to a second surface of the connector body, wherein the second surface of the connector body is adjacent to the first engaging member 68. The through bore 57 houses the first locking member, which comprises a first locking nut 70 for securing an elongate member within the first engaging member 68.

In some embodiments, the first engaging member 68 may be a hooked end configured to accept an elongate member such as a spinal rod. In other embodiments, the first engaging member 68 may have a different design that is compatible with other types of elongate members, such as polygonal bars or I-beams. In some embodiments, the first locking nut 70 can secure the elongate member by pushing the elongate member against the first engaging member 68.

In some embodiments, the first locking member 63 may further comprise a first contacting saddle 69 configured to make contact with and secure an elongate member in the first engaging member 68. In some embodiments, the surface 69a of the first contacting saddle 69 that contacts the first locking nut 70 has a helical surface, which corresponds with the helical surface on the bottom surface 70b of the first locking nut 70. In other embodiments, the complimentary surfaces are contours other than helical. In some embodiments, turning the first locking nut 70 may cause the contacting saddle 69b to push down on the elongate member, thereby securing the elongate member to the first connector body 62 in the engaging member 68.

In some embodiments, the first locking member 63 is configured to secure both the articulation (i.e., lock the pivot joint 73 of the transverse rod 64) and the first elongate member 54 to the first connector body 62. The first connector body 62 may also comprise a passage 72 that has one opening toward the medial end and the other opening in the through bore 57. The passage 72 houses the pushing member 71 and the pivot joint end of the transverse rod 64. In some embodiments, the pivot joint 73 comprises a cylindrical shape with a longitudinal axis 74 that is generally perpendicular to the longitudinal axis 58 of the transverse rod 64. The projection end 75 extends out from the medial opening of the passage 72 in the first connector body 62. In some embodiments, the medial opening of the passage 72 is configured to permit the transverse rod 64 to pivot at the pivot joint 73 about the longitudinal axis 74 of the pivot joint when the first locking member 63 is in an unlocked position, creating an angle α measured between the longitudinal axis 58 of the transverse rod 64 and the longitudinal axis 59 of the first connector body 62, as illustrated in FIG. 5. For example, the medial opening may be larger than the diameter of the transverse rod 64, particularly in the lateral directions, to allow the transverse rod 64 to swing from one side to the other along the defined plane. This pivoting movement allows the transverse connector 53 to adjust for convergence or divergence of the implanted elongate members 54 and 56. In some embodiments, the pivot joint 73 may comprise other configurations that permit the transverse rod 64 to pivot along a different plane.

In some embodiments, the pushing member 71 can be coupled to both the pivot joint 73 of the transverse rod 64 within the passage 72 and the first locking nut 70 through the opening in the through bore 57. In some embodiments, the surface of the pushing member 71 that contacts the first locking nut 70 can have a helical surface complimentary to the second helical surface on the first locking nut 70. The helical surfaces can be configured so that as the locking nut 70 is turned to the lock position, the pushing member 71 pushes the pivot joint 73 up and medially to lock the pivot joint 73 against the interior wall of the passage 72 in the first connector body 62. In other embodiments, the complimentary surfaces can be contours other than helical.

For example, in some embodiments, the first locking nut 70 can have a cam surface disposed on the outer cylindrical surface 70c which couples with the pushing member 71. The cam surface can have a radial gradient wherein the radius of the cam surface can increase from one side of the cam surface to the other side of the cam surface. When the first locking nut 70 is rotated, the increasing radius of the cam surface can push the pushing member 71 in the medial direction, thereby translating rotational motion of the first locking nut 70 into linear movement of the pushing member 71.

The pushing member 71 can have a generally trapezoidal wedge configuration with coupling surfaces for the first locking nut 70 and the pivot joint 73. In some embodiments, the pushing member 71 can have a slot disposed along the lateral direction that extends from the top of the pushing member 71 down to a partial height of the pushing member 71. When the first locking nut 70 biases the pushing member 71 against the pivot joint 73, the slotted pushing member 71 can partially deform to provide a spring force to the pivot joint 73. In other embodiments, the slot in the pushing member 71 can be omitted.

In some embodiments, the pivot joint 73 can have a roughened surface on at least a portion of its surface that contacts a complimentary surface on the first connector body 62 when the first locking nut 70 is tightened or in the locked position. Some examples of the roughened surface include, but are not limited to teeth, ridges, or abrasive surfaces. When the first locking nut 70 is tightened or locked, the transverse rod 64 is fixed and can no longer pivot along the defined plane.

In some embodiments, the pivot joint 73 can comprise elongate teeth or grooves that are disposed along the longitudinal axis 74 on at least a portion of the cylindrical surfaces that contacts the first connector body 62. The first connector body 62 can comprise a complimentary surface with elongate teeth or grooves that can couple with the elongate teeth or grooves on the pivot joint 73 to restrict the pivotal movement of the transverse rod 64. In other embodiments, the elongate teeth or grooves may be omitted from the pivot joint 73.

Figure 8:
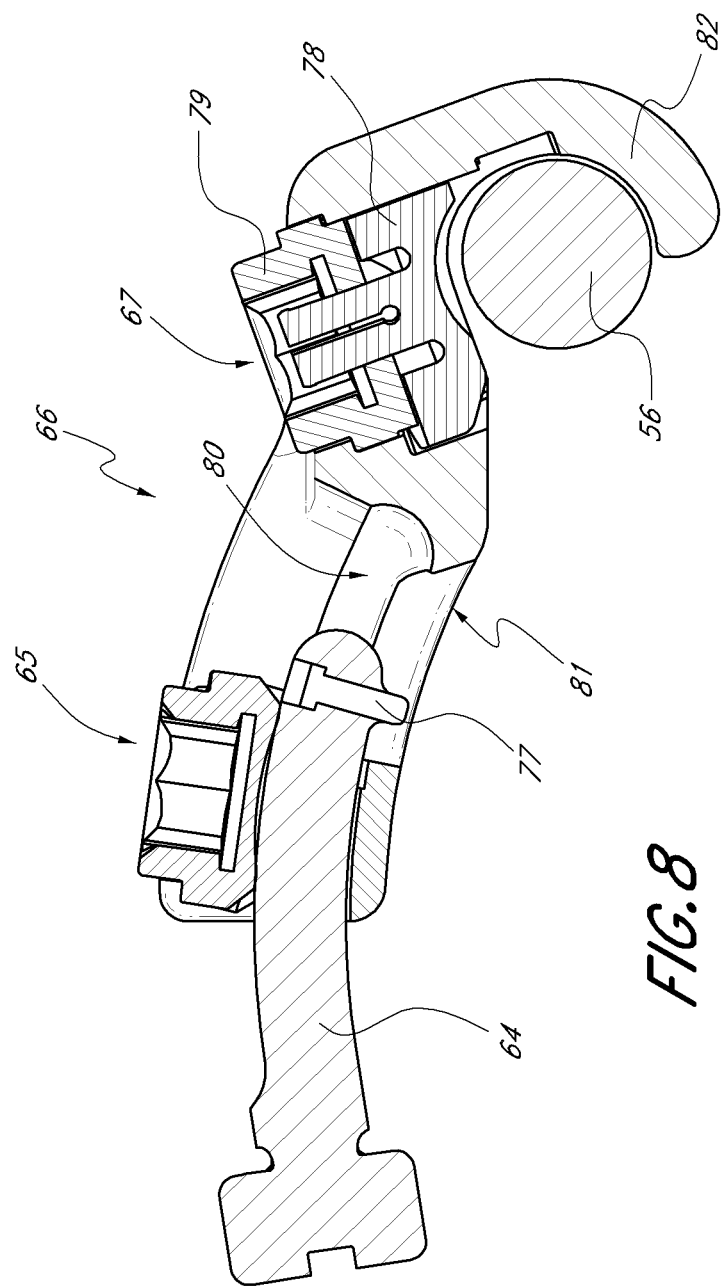
FIG. 8 is a cross-sectional view of one embodiment of an adjustable transverse connector showing a rod connector with a second locking member and a transverse rod with a third locking member.

As shown in FIG. 8, the second connector body 66 comprises a second locking member 67, a third locking member 65 and a second engaging member 82. The second connector body 66 comprises a receiving bore 80 that has an opening at the medial end of the second connector body 66. The receiving bore 80 is configured to receive the projection end 75 of the transverse rod 64, which allows the second connector body 66 to slide along generally the longitudinal axis 58 of the transverse rod 64 to account for variations in implanted distances of elongate members 54 and 56. In some embodiments, the second connector body 66 can also rotate generally about the longitudinal axis 58 to account for non-parallel and/or non co-planar elongate members 54 and 56.

In some embodiments, the transverse rod 64 is allowed to slide in and out of the receiving bore 80 along generally the longitudinal axis 58 of the transverse rod 64 so as to lengthen and shorten the overall length of the transverse connector 53. In some embodiments, the transverse rod 64 may also rotate within the receiving bore 80 generally about the longitudinal axis 58. In some embodiments, the transverse rod 64 further comprises a retaining pin 77 toward the end of the projection end 75 as shown in FIG. 8. The retaining pin 77 serves to stop the transverse rod 64 from sliding out of the receiving bore 80 completely and limits the rotation of the transverse rod 64 within the receiving bore 80 about axis 58. As an inseparable piece, the transverse connector 53 is easier to handle and to implant without having to account for several small pieces.

Figure 9:
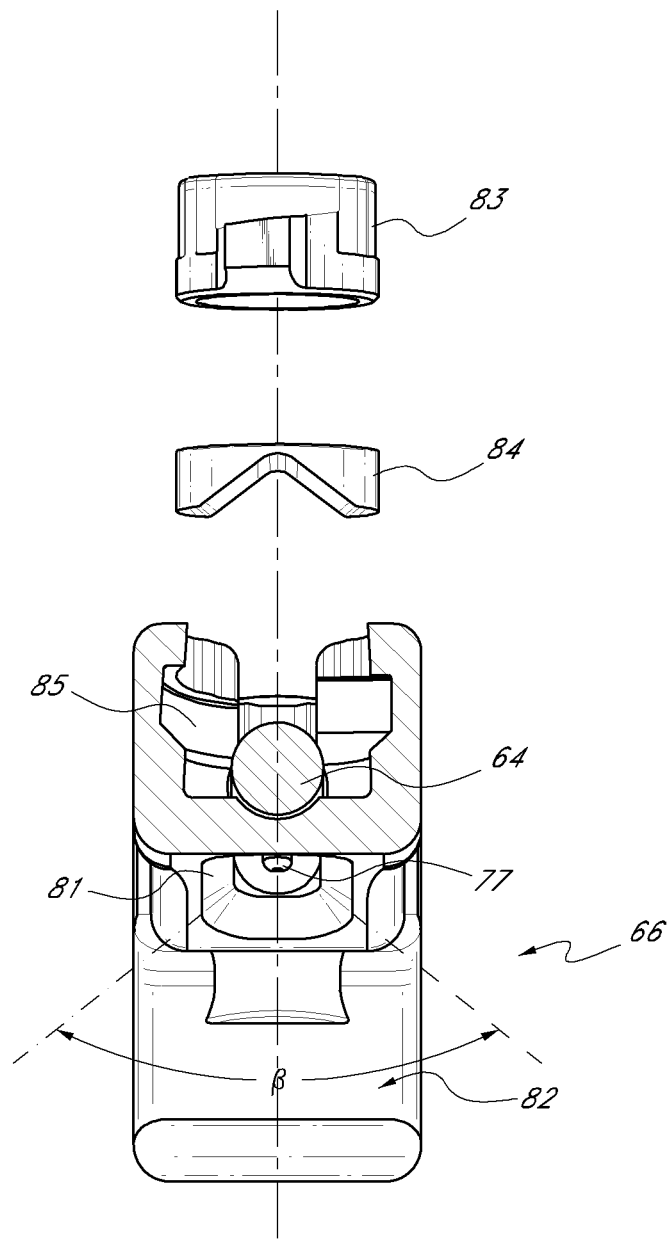
FIG. 9 is a cross-sectional exploded view of one embodiment of a slideable and rotational transverse rod with a third locking member.

With reference to FIGS. 8 and 9, in some embodiments, the retaining pin 77 may be engaged in a groove 81 located on the underside of the second connector body 66. In some embodiments, the groove 81 is an elongated cutout that is large enough to allow the movement of the retaining pin 77 when the transverse rod 64 slides and rotates inside of the receiving bore 80. In some embodiments, the groove 81 may also be a recess within a portion of the receiving bore that is large enough to accommodate retaining pin 77 movements. The angle of rotation allowed by the groove 81 is labeled as β in FIG. 9. In some embodiments, about a 90 degree freedom of rotation of the transverse rod 64 is sufficient to account for angular variations of non-parallel connector rods in the usual clinical environment. However, groove sizes that allow for less or more than 90 degrees of rotation of the transverse rod 64 may be appropriate for some situations.

The second connector body 66 also comprises a first through bore from a first surface of the connector body to a second surface of the connector body, wherein the opening of the second through bore on the second surface of the connector body is adjacent to the second engaging member 82. The first through bore of the second connector body 66 houses the second locking member 67, which comprises a second locking nut 79 for securing a second elongate member 56 within the second engaging member 82.

In some embodiments, the second engaging member 82 may be a hooked end configured to accept an elongate member such as a spinal rod. In other embodiments, the second engaging member 82 may have a different design that is compatible with other types of elongate members, such as polygonal bars or I-beams. In some embodiments, the second locking nut 79 can secure the second elongate member 56 by pushing the elongate member against the second engaging member 82.

In some embodiments, the second locking member 67 may further comprise a second contacting saddle 78 configured to make contact with and secure the second elongate member 56 in the second engaging member 82. The surface of the second contacting saddle 78 that contacts the second locking nut 79 has a helical surface, which is complimentary to the helical surface on the bottom surface of the second locking nut 79. In other embodiments, the complimentary surfaces are contours other than helical. In some embodiments, turning the second locking nut 79 to a locked position may cause the contacting saddle 78 to push down on the second elongate member 56, thereby securing the second elongate member 56 to the second connector body 66 in the second engaging member 82.

With reference to FIGS. 6, 8 and 9, the second connector body 66 further comprises a second through bore 85 from the first surface of the connector body to the receiving bore 80 at the medial end of the second connector body 66. The second through bore 85 of the second connector body 66 houses the third locking member 65. The third locking member 65 comprises a third locking nut 83, which is configured to secure the transverse rod 64 to the second connector body 66. Once the length and axial rotation of the transverse rod 64 are positioned within the receiving bore 80, the transverse rod 64 can be locked by tightening the third locking nut 83.

In some embodiments, the third locking member 65 may further comprise a transverse rod contacting saddle 84. In some embodiments, the third locking nut 83 is a cylindrical body with a helical surface on its outer cylindrical wall which, when tightened or locked, contacts a complimentary helical surface on the second connector body 66 causing the third locking nut 83 to apply pressure against the transverse rod contacting saddle 84, which in turn applies pressure to the transverse rod 64, locking it in place. In other embodiments, the complimentary surfaces are contours other than helical. In some embodiments, the transverse rod contacting saddle 84 is a cylindrical body with a concave surface on one end for accepting and locking the transverse rod 64 in a fixed position and a flat surface on the other end for mating with the bottom flat surface of the third locking nut 83. In other embodiments, the transverse rod contacting saddle 84 may be omitted and the third locking nut 83 can be in contact with the transverse rod 64. The third locking nut 83 can apply pressure directly to the transverse rod 64. In some embodiments, the bottom surface of the third locking nut 83 can be spherically concave to optimize contact area with the curved transverse rod 64.

In some embodiments, the top 70a of at least one of the locking nuts comprise a mating surface for accepting common tools, such as Allen wrench, screwdrivers, or any other common tool. In other embodiments, at least one locking nuts comprise a special mating surface on top that can only be operated by a special tool. In some embodiments, one or more of the contacting saddles may comprise a stem extending from the top portion 69a. In these embodiments, the corresponding locking nut would have a hole to accommodate the protruding stem on the contacting saddle, so the contacting saddle is properly lined up with the corresponding locking nut. In some embodiments, the configurations of the locking nuts and the contacting saddles may be interchangeable. For example, the complimentary helical surfaces may be on the outer cylindrical wall 70c of the locking nut and the connector body in one embodiment. In another embodiment, the complimentary helical surfaces may be on the bottom 70b of the locking nut and the top 69a of the corresponding contacting saddle. In some embodiments, at least one of the locking nuts and/or contacting saddles may have a different configuration compared to the others.

C. Implantation Procedure

In some embodiments of the invention, the patient is intubated and general anesthesia is achieved. The patient is prepped and draped in the usual sterile fashion. A posterior approach to the spine is used to expose the posterior vertebral bodies. Many posterior approaches to the vertebral column are described in various medical texts such as Campbell's Operative Orthopaedics, 10th ed., edited by Canale et al., herein incorporated by reference. In some embodiments, the upper cervical spine is accessed. In other embodiments, the lower cervical spine, cervicothoracic junction, thoracic spine, thoracolumbar junction, lumbar region, lumbosacral junction, sacrum or combination of the above regions are accessed.

The vertebral column is accessed and one or more vertebrae are identified and accessed. In some embodiments, two or more vertebrae are accessed and in still other embodiments, two or more adjacent vertebrae are accessed. A pedicle screw, hook, anchor or other attachment device is attached to a first vertebra. A second attachment device is attached to a second vertebra. The two attachment devices are coupled with a first elongate member 54. In some cases, a second set of attachment devices is then attached to the same vertebrae on the other side of the posterior arch. In other cases, the second set of attachment devices can be attached to different vertebrae. A second elongate member 56 is then used to couple the second set of attachment devices. In some cases, the two elongate members 54, 56 are generally parallel to each other. In other cases, the two elongate members 54, 56 may be at an angle to each other or unleveled.

A transverse connector 53, such as one of the embodiments disclosed in the present application, is positioned between the two elongate members 54, 56. The transverse connector 53 can be bent at the articulation between the first connector body 62 and the transverse rod 64 to compensate for convergence or divergence between the two elongate members 54, 56. The projection end 75 of the transverse rod 64 can be rotated within the receiving bore 80 in the second connector body 66 to compensate for the differences in angular orientations of the two elongate members 54, 56 with respect to coronal plane. The transverse rod 64 can also be slideably moved in and out of the receiving bore 80 for adjusting the bridging distance between the two elongate members 54, 56.

After adjustments are made to properly seat the elongate members 54, 56 into the engaging members 68, 82 of the transverse connector 53, the first and the second locking members 63, 67 are tightened to secure the elongate members 54, 56 to the transverse connector 53. At the same time, the articulation between the first connector body 62 and the transverse rod 64 is also secured or locked at the set angle. The third locking member 65 is also tightened to secure the transverse rod 64 to the second connector body 66 and to lock down the rotational and the sliding movements, so the longitudinal length of the transverse connector 53 and the angular orientation of the two connector bodies are fixed. Lastly, the operative site is irrigated with antibiotics and the operative field is sutured closed.

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A transverse connector for vertebral fixation systems comprising:
    a first connector body comprising a first engaging member for engaging a first elongate member, and a first locking member;
    a second connector body comprising a second engaging member for engaging a second elongate member;
    a transverse rod coupled to the first connector body and the second connector body;
    a pivot joint disposed on a first end of the transverse rod and configured to couple with the first connector body; and
    a pushing member housed in the first connector body, wherein the first locking member is configured to contact the pushing member, and the pushing member is configured to contact the transverse rod, wherein the pushing member is deformable;
    wherein in a locked configuration, a side surface of the first locking member pushes the pushing member medially to lock the pivot joint against the first connector body and a bottom surface of the first locking member pushes the first elongate member against the first engaging member.

2. The transverse connector of claim 1, wherein the first locking member comprises:
    a first locking nut with a top surface, a bottom surface, and a side surface, and
    a first contacting saddle with a top surface corresponding to the bottom surface of the first locking nut and a bottom surface corresponding to a surface of the first elongate member.

3. The transverse connector of claim 2, wherein in the locked configuration, the side surface of the first locking nut pushes on the pushing member, the bottom surface of the first locking nut pushes on the top surface of the first contacting saddle, and the bottom surface of the first contacting saddle pushes on the first elongate member.

4. The transverse connector of claim 1, wherein in a locked position, the side surface of the first locking member pushes against the pushing member to compress a slot.

5. The transverse connector of claim 1, wherein the pushing member comprises a slot.

6. The transverse connector of claim 5, wherein the slot extends from the top of the pushing member down to a partial height of the pushing member.

7. The transverse connector of claim 5, wherein in the locked position, the pushing member partially deforms to provide a spring force to the transverse rod.

8. The transverse connector of claim 1, further comprising a second locking member, wherein the second locking member is configured to push the second elongate member against the second engaging member.

9. The transverse connector of claim 1, further comprising a third locking member configured to secure the transverse rod to the second connector body.

10. The transverse connector of claim 1, wherein the second connector body further comprises a receiving bore configured to receive a projection end of the transverse rod.

11. The transverse connector of claim 10, wherein the transverse rod can slideably move in and out of the receiving bore along a longitudinal axis of the second connector body.

12. The transverse connector of claim 10, further comprising a stop configured to prevent the transverse rod from sliding out of the second connector body.

13. The transverse connector of claim 1, further comprising:
    a first coupling surface on a portion of the pivot joint; and
    a second coupling surface on a portion of the first connector body;
    wherein, when the first and second coupling surfaces are coupled, the transverse rod and the first connector body maintain an angular orientation in relation to each other.

14. The transverse connector of claim 13, wherein the coupling surfaces comprise teeth.

15. A transverse connector for vertebral fixation systems comprising:
    a first connector body comprising a first end for engaging a first elongate member, a first locking member, and a pushing member;
    a second connector body comprising a second end for engaging a second elongate member;
    a transverse rod, a first end of the transverse rod configured to couple with the first connector body and be retained within the first connector body, a second end of the transverse rod configured to couple with the second connector body and be retained within the second connector body;
    wherein the first locking member has a locked position and an unlocked position, wherein in the unlocked position the transverse rod pivots and translates within the first connector body, wherein in the locked position, the first locking member pushes and compresses the pushing member against the transverse rod and the transverse rod pushes against the first connector body to prevent the transverse rod from pivoting and translating within the first connector body, and wherein in the locked position, the first locking member pushes against the first elongate member and the first elongate member pushes against the first end of the first connector body.

16. The transverse connector of claim 15, wherein the pushing member is deformable.

17. The transverse connector of claim 15, wherein the pushing member comprises a slot.

18. The transverse connector of claim 17, wherein the slot extends from the top of the pushing member down to a partial height of the pushing member.

19. The transverse connector of claim 17, wherein in the locked position, the pushing member partially deforms to provide a spring force to the transverse rod.

\* \* \* \* \*